US011400042B2

(12) United States Patent
Ronchard et al.

(10) Patent No.: US 11,400,042 B2
(45) Date of Patent: *Aug. 2, 2022

(54) PROCESS FOR TREATING KERATIN FIBRES, COMPRISING THE APPLICATION OF A COMPOSITION COMPRISING UREA OR A DERIVATIVE THEREOF, A POLYOL AND AN AMINO SILICONE

(71) Applicant: L'OREAL, Paris (FR)

(72) Inventors: Guillaume Ronchard, Saint-Chamond (FR); Manon Chaumontet, Paris (FR); Renaud Souchay, Le Plessis-Bouchard (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/064,310

(22) PCT Filed: Dec. 22, 2016

(86) PCT No.: PCT/EP2016/082371
§ 371 (c)(1),
(2) Date: Jun. 20, 2018

(87) PCT Pub. No.: WO2017/109067
PCT Pub. Date: Jun. 29, 2017

(65) Prior Publication Data
US 2019/0021983 A1    Jan. 24, 2019

(30) Foreign Application Priority Data

Dec. 23, 2015  (FR) ...................................... 1563195

(51) Int. Cl.
| A61K 8/898 | (2006.01) |
| A61K 8/34  | (2006.01) |
| A61K 8/42  | (2006.01) |
| A61Q 5/04  | (2006.01) |
| A45D 7/06  | (2006.01) |

(52) U.S. Cl.
CPC ................ *A61K 8/898* (2013.01); *A45D 7/06* (2013.01); *A61K 8/345* (2013.01); *A61K 8/42* (2013.01); *A61Q 5/04* (2013.01)

(58) Field of Classification Search
None
See application file for complete search history.

(56) References Cited

U.S. PATENT DOCUMENTS

| 3,654,936 | A  | 4/1972  | Wajaroff |
| 4,131,576 | A  | 12/1978 | Iovine et al. |
| 5,635,170 | A  | 6/1997  | Lang et al. |
| 8,765,107 | B2 | 7/2014  | Philippe et al. |
| 2005/0102768 | A1 | 5/2005 | Bartolone et al. |
| 2008/0025939 | A1* | 1/2008 | Cassier .................... A61Q 5/04 424/70.5 |
| 2010/0028280 | A1* | 2/2010 | Philippe ................. A61K 8/365 424/70.2 |

FOREIGN PATENT DOCUMENTS

| EP | 0095238 A2 | 11/1983 |
| EP | 1880706 A1 | 1/2008 |
| EP | 1880707 A1 | 1/2008 |
| EP | 1880708 A1 | 1/2008 |
| EP | 1880709 A1 | 1/2008 |
| EP | 1880710 A1 | 1/2008 |
| FR | 3004934 A1 | 10/2014 |
| JP | 2009-132625 A | 6/2009 |
| JP | 2010-070526 A | 4/2010 |
| JP | 2014-177438 A | 9/2014 |
| JP | 2016-017069 A | 2/2016 |
| JP | 2016-113384 A | 6/2016 |
| RU | 2007995 C1 | 2/1994 |
| WO | 2007/135297 A2 | 11/2007 |
| WO | 2012/027369 A2 | 3/2012 |
| WO | 2012/099110 A1 | 7/2012 |
| WO | 2013098332 A2 | 7/2013 |
| WO | 2018/000059 A1 | 1/2018 |

OTHER PUBLICATIONS

Japanese Office Action for counterpart Application No. 2018-533120, dated May 7, 2019, English Translation.
International Search Report for Application No. PCT/EP2016/082371, dated Feb. 27, 2017.
International Search Report for counterpart Application No. PCT/BR2016/050151, dated Oct. 19, 2016.
International Preliminary Report on Patentability for counterpart Application No. PCT/BR2016/050151, dated Mar. 28, 2018.
Non-Final Office Action for co-pending U.S. Appl. No. 16/313,702, dated Oct. 10, 2019.
Final Office Action for co-pending U.S. Appl. No. 16/313,702, dated Feb. 10, 2020.
Non-Final Office Action for copending U.S. Appl. No. 16/313,702, dated Jul. 13, 2020.
Final Office Action for copending U.S. Appl. No. 16/313,702, dated Feb. 10, 2021.
Pal et al., "Microwave-assisted synthesis of silver nanoparticles using ethanol as a reducing agent," Materials Chemistry and Physics, 114, (2009), pp. 530-532.

\* cited by examiner

*Primary Examiner* — Melissa L Fisher
(74) *Attorney, Agent, or Firm* — The Marbury Law Group, PLLC

(57) ABSTRACT

The present invention relates to a process for treating keratin fibres, in particular human keratin fibres such as the hair, comprising: 1) a step of applying to the keratin fibres a composition comprising: a) one or more compounds chosen from urea and/or urea derivatives, b) one or more polyols, c) one or more amino silicones, 2) a step of heat treatment of the keratin fibres, the heat treatment step 2) preferably being after step 1). The present invention also relates to a composition that may be used in the process according to the invention.

15 Claims, 1 Drawing Sheet

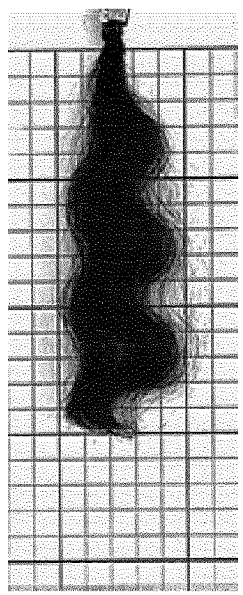
T
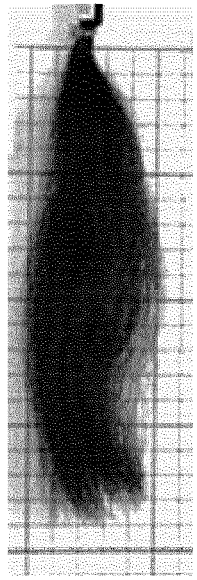
D₁
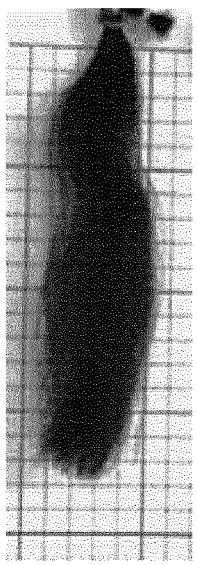
D₁₀
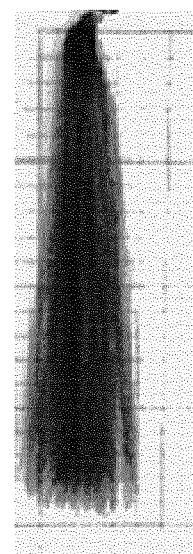
E₁
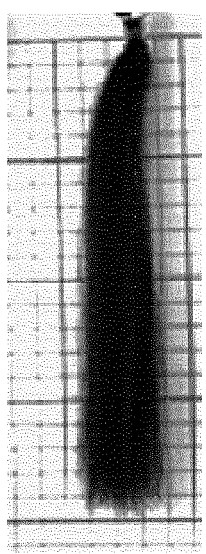
E₁₀

PROCESS FOR TREATING KERATIN FIBRES, COMPRISING THE APPLICATION OF A COMPOSITION COMPRISING UREA OR A DERIVATIVE THEREOF, A POLYOL AND AN AMINO SILICONE

CROSS REFERENCE TO RELATED APPLICATIONS

This is a national stage application of PCT/EP2016/082371, filed internationally on Dec. 22, 2016, which claims priority to French Application No. 1563195, filed on Dec. 23, 2015, both of which are incorporated by reference herein in their entireties.

The present invention relates to a process for treating keratin fibres, in particular human keratin fibres such as the hair, comprising a step of applying to the keratin fibres a composition, especially a cosmetic composition, comprising urea and/or derivatives thereof, one or more polyols and one or more amino silicones, and a step of heat treatment of the keratin fibres.

The present invention also relates to a composition comprising urea and/or derivatives thereof, one or more polyols and one or more amino silicones.

Many people are dissatisfied with the appearance of their hair; in particular, people who have curly hair usually wish to obtain straight hair.

The processes for straightening or relaxing the hair generally involve reducing agents based on thiol or strong alkaline agents.

These two techniques are based on cleavage of the disulfide covalent bonds present in keratin.

The first technique consists, in a first stage, in opening the disulfide bonds using a composition comprising a reducing agent, and then, in a second stage, after having generally rinsed the hair, in reconstituting said disulfide bonds by applying to the hair, which has been placed beforehand under tension, for example by means of rollers, an oxidizing composition also known as a "fixer" (fixing step), so as to give the head of hair the desired shape.

The second technique consists in performing a lanthionization operation, using a composition containing a base belonging to the hydroxide family. Contrary to the first one, this second technique does not require a fixing step, since the formation of the lanthionine bonds is irreversible. Thus, this technique makes it possible, without preference, to perform waving, relaxing, uncurling or straightening of the hair. In particular, it is mainly used for relaxing naturally curly hair.

However, these two techniques have many drawbacks. In particular, they lead to unpleasant odours during their use, a certain level of discomfort of the scalp and substantial degradation of the keratin fibres.

More recently, another technique has been developed, which consists in combining a heat treatment step and a step of applying a composition comprising formaldehyde. This technique is particularly effective for imparting a better appearance to damaged hair and/or for treating long hair and curly hair.

Formaldehyde, subjected to a temperature that may be up to 200° C. or more, for example by means of an iron, crosslinks the proteins of the keratin fibres by reaction on their nucleophilic sites.

However, it is sought to avoid the use of substances such as formaldehyde, which may prove to be irritant or even highly toxic.

Consequently, there is a need to provide novel solutions for straightening keratin fibres, in particular human keratin fibres such as the hair, which make it possible to obtain good curl relaxation and good volume control, and which are long-lasting, non-irritant and non-toxic.

Furthermore, these novel solutions must provide care to keratin fibres and protection of keratin fibres against heat, in particular at their ends.

It has been discovered, surprisingly, that a process for treating keratin fibres, in particular human keratin fibres such as the hair, comprising a step of applying to the keratin fibres a composition comprising urea and/or derivatives thereof, one or more polyols and one or more amino silicones, and a step of heat treatment of the keratin fibres, makes it possible to satisfy the technical problem posed above.

Consequently, one subject of the present invention relates to a process for treating keratin fibres, in particular human keratin fibres such as the hair, comprising:
1) a step of applying to the keratin fibres a composition comprising:
   a) one or more compounds chosen from urea and/or urea derivatives,
   b) one or more polyols,
   c) one or more amino silicones,
2) a step of heat treatment of the keratin fibres, the heat treatment step 2) preferably being after step 1).

The process according to the invention makes it possible, in particular, to straighten the hair and to obtain hair that has good curl relaxation and better volume control.

Furthermore, the process according to the invention makes it possible, in particular, to obtain long-lasting straightening that withstands several shampoo washes.

Finally, the process according to the invention provides care to keratin fibres and protection of keratin fibres against heat, in particular at their ends.

Another subject of the invention is a composition comprising:
   a) one or more compounds chosen from urea and/or urea derivatives, preferably present in a content ranging from 1% to 15% by weight, relative to the total weight of the composition,
   b) one or more polyols,
   c) one or more amino silicones, preferably present in a content ranging from 0.1% to 4% by weight, relative to the total weight of the composition,
   the compound(s) b)/compound(s) a) weight ratio preferably being greater than or equal to 0.5.

The composition according to the invention is in particular able to be used in the process according to the invention.

Other characteristics and advantages of the invention will emerge more clearly on reading the description and the examples that follow and on reading the single figure which corresponds to pictures of locks of hair without treatment (picture T), treated with a comparative process (pictures D1 and D10) and treated with a process according to the invention (pictures E1 and E10).

Preferably, the process for treating keratin fibres according to the invention is a process for straightening keratin fibres, in particular human keratin fibres such as the hair.

As indicated previously, the process according to the invention comprises a step of applying to the keratin fibres a composition comprising:
   a) one or more compounds chosen from urea and/or urea derivatives,
   b) one or more polyols,
   c) one or more amino silicones.

For the purposes of the present invention, the term "urea derivative" means any compound other than urea $CO(NH_2)_2$ itself, comprising in its chemical formula a carbonyl group simply bonded to two nitrogen atoms, i.e. a unit

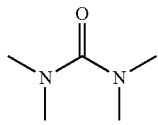

Preferably, said compound(s) a) are chosen from the compounds of formula (I) or (II), salts thereof or hydrates thereof:

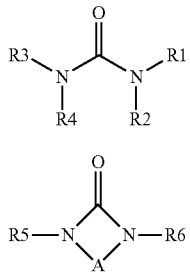

in which:

R1, R2, R3 and R4 represent, independently:
(i) a hydrogen atom or
(ii) a linear or branched, cyclic or acyclic $C_1$-$C_5$ lower alkyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, ($C_1$-$C_4$)alkyl, (di)($C_1$-$C_4$)(alkyl)amino, preferably dimethylamino, carboxyl, halogen, $C_6$-$C_{18}$ aryl, carboxamide and N-methylcarboxamide;

it being understood that:
when R1, R2 and R3 represent a hydrogen atom, R4 may denote a radical from among: carboxamide, methoxy, ethoxy, 1,2,4-triazolyl, cyclopentyl, ($C_1$-$C_6$)alkylcarbonyl such as acetyl, ($C_1$-$C_6$)alkoxycarbonyl such as methoxycarbonyl or ethoxycarbonyl, CO—CH═CH—COOH, phenyl optionally substituted with a chlorine atom or a hydroxyl, benzyl or 2,5-dioxo-4-imidazolidinyl radical;
when R1 and R3 represent a hydrogen atom, R2 may represent a hydrogen atom or a methyl or ethyl radical and R4 may represent an acetyl radical;
when R1=R2=H, R3 and R4 can form, with the nitrogen atom that bears them, a 5- or 6-membered ring such as a piperidine, 3-methylpyrazole, 3,5-dimethylpyrazole or maleimide ring;
R1 and R2 and also R3 and R4 can form, with the nitrogen atom that bears them, an imidazole ring;
R5 and R6 represent, independently of each other:
(iii) a hydrogen atom or
(iv) a linear or branched, cyclic or acyclic $C_1$-$C_5$ lower alkyl, acyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, amino, dimethylamino, carboxyl, halogen, $C_6$-$C_{18}$ aryl, carboxamide and N-methylcarboxamide;

A is a radical chosen from the following radicals: $CH_2$—$CH_2$, CH═CH, $CH_2$—CO, CO—NH, CH═N, CO—CO, CHOH—CHOH, (HOOC)CH—CH, CHOH—CO, $CH_2$—$CH_2$—$CH_2$, $CH_2$—NH—CO, CH═C($CH_3$)—CO, NH—CO—NH, $CH_2$—$CH_2$—CO, $CH_2$—N($CH_3$)—$CH_2$, NH—$CH_2$—NH, CO—CH($CH_3$)—$CH_2$, CO—$CH_2$—CO, CO—NH—CO, CO—CH(COOH)—$CH_2$, CO—CH═C(COOH), CO—CH═C($CH_3$), CO—C($NH_2$)═CH, CO—C($CH_3$)═N, CO—CH═CH, CO—CH═N and CO—N═CH.

In a first particular embodiment of the invention, said compound(s) a) are of formula (I) and are chosen from:
urea
methylurea
ethylurea
propylurea
n-butylurea
sec-butylurea
isobutylurea
tert-butylurea
cyclopentylurea
ethoxyurea
hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleamide
N-carbamoylmaleamic acid
piperidinecarboxamide
1,2,4-triazol-4-ylurea
hydantoic acid
methyl allophanate
ethyl allophanate
acetylurea
hydroxyethyleneurea
2-(hydroxyethyl)ethyleneurea
diallylurea
chloroethylurea
N,N-dimethylurea
N,N-diethylurea
N,N-dipropylurea
cyclopentyl-1-methylurea
1,3-dimethylurea
1,3-diethylurea
1,3-bis(2-hydroxyethyl)urea
1,3-bis(2-hydroxypropyl)urea
1,3-bis(3-hydroxypropyl)urea
1,3-dipropylurea
ethyl-3-propylurea
sec-butyl-3-methylurea
isobutyl-3-methylurea
cyclopentyl-3-methylurea
N-acetyl-N'-methylurea
trimethylurea
butyl-3,3-dimethylurea
tetramethylurea and
a mixture of these compounds.

In a second particular embodiment of the invention, said compound(s) a) are of formula (II) and are chosen from:
parabanic acid
1,2-dihydro-3H-1,2,4-triazol-2-one
barbituric acid
uracil 1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidone
1-methyl-2-imidazolidinone
1,3-dimethyl-2-imidazolidinone
4,5-dihydroxyimidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-N-propylhydantoin
5-ethyl-5-methylhydantoin
5-hydroxy-5-methylhydantoin
5-hydroxymethylhydantoin
1-allylhydantoin
1-aminohydantoin
hydantoin-5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
1,3-dimethylbarbituric acid
cyanuric acid
1-methylhexahydropyrimidine-2,4-dione
1,3-dimethyl-3,4,5,6-tetrahydro-2-(1H)-pyrimidinone
5-(hydroxymethyl-2,4-(1H,3H)-pyrimidinedione
2,4-dihydroxypyrimidine-5-carboxylic acid
6-azathymine
5-methyl-1,3,5-triazinan-2-one
N-carbamoylmaleamic acid and
alloxan monohydrate and
a mixture of these compounds.

Most particularly preferably, said compound(s) a) are chosen from urea, hydroxyethylurea and a mixture of these compounds.

Said compound(s) a) preferably represent from 1% to 15% by weight and more preferentially from 2% to 12% by weight, relative to the total weight of the composition.

The composition that may be used in the process according to the invention also comprises one or more polyols.

For the purposes of the present invention, the term "polyol" means an organic compound comprising at least two hydroxyl groups (—OH), borne by different carbon atoms, this compound possibly being aliphatic, acyclic, linear or branched.

More particularly, the polyol(s) that may be used according to the invention comprise from 2 to 30 hydroxyl groups, more preferentially from 2 to 10 hydroxyl groups and even more preferentially from 2 to 3 hydroxyl groups.

The polyol(s) that may be used according to the invention generally comprise at least three carbon atoms.

Preferably, said polyol(s) that may be used according to the invention (compound(s) b)) are chosen from polyols comprising at least three carbon atoms and ethylene glycol, and preferably said compound(s) b) are chosen from propylene glycol, 1,3-propanediol, 1,3-butylene glycol, 1,2-pentanediol, dipropylene glycol, hexylene glycol, pentylene glycol, glycerol, ethylene glycol, and a mixture of these compounds, and more preferentially said compound(s) b) are chosen from propylene glycol, 1,3-propanediol and a mixture of these compounds.

In the composition that may be used according to the invention, said compound(s) b) preferably represent from 1% to 30% by weight and more preferentially from 2% to 15% by weight, relative to the total weight of the composition.

Preferably, in the composition that may be used in the process according to the invention, the compound(s) b)/compound(s) a) weight ratio is greater than or equal to 0.5, more preferentially greater than or equal to 1.

The composition that may be used in the process according to the invention also comprises one or more amino silicones (compound(s) c)).

For the purposes of the present invention, the term "amino silicone" means any silicone comprising at least one primary, secondary or tertiary amine function or a quaternary ammonium group.

Preferably, the amino silicone(s) of the composition that may be used in the process according to the invention comprise in their structure at least four silicon atoms.

Throughout the text hereinbelow, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and constituted essentially of a repetition of main units in which the silicon atoms are linked together via oxygen atoms (siloxane bond —Si—O—Si—), optionally substituted hydrocarbon-based groups being directly linked via a carbon atom to said silicon atoms. The hydrocarbon-based groups that are the most common are alkyl groups, especially of $C_1$-$C_{10}$, and in particular methyl, fluoroalkyl groups, the alkyl part of which is of $C_1$-$C_{10}$, and aryl groups and in particular phenyl.

The amino silicones of the composition that may be used in the process according to the invention may be chosen from the silicones (a) to (f) below:

(a) the compounds corresponding to formula (III) below:

$$(R_1)_a(T)_{3-a}\text{-Si}[\text{OSi}(T)_2]_n\text{—}[\text{OSi}(T)_b(R_1)_{2-b}]_m\text{—OSi}(T)_{3-a}\text{-}(R_1)_a \quad (III)$$

in which formula (III):
T represents a hydrogen atom or a phenyl, hydroxyl (—OH) or $C_1$-$C_8$ alkyl group, and preferably methyl, or a $C_1$-$C_8$ alkoxy, preferably methoxy,
a denotes the number 0 or an integer from 1 to 3, and preferably 0,
b denotes 0 or 1, and in particular 1,
m and n are integers such that the sum (n+m) can range especially from 1 to 2000 and in particular from 50 to 150, n possibly denoting a number from 0 to 1999 and especially from 49 to 149, and m possibly denoting a number from 1 to 2000 and especially from 1 to 10,
$R_1$ is a monovalent group of formula —$C_qH_{2q}L$ in which q is an integer from 2 to 8 inclusive and L is an optionally quaternized amino group chosen from the following groups:
—N($R_2$)—$CH_2$—$CH_2$—N($R_8$)$_2$,
—N($R_2$)$_2$,
—N$^+$($R_2$)$_3$Q$^-$,
—N$^+$($R_2$)$_2$(H)$_2$Q$^-$,
N($R_2$)$_2$HQ$^-$,
—N($R_2$)—$CH_2$—$CH_2$—N$^+$($R_2$)(H)$_2$Q$^-$,
in which $R_2$ may denote a hydrogen atom, a phenyl group, a benzyl group or a saturated monovalent hydrocarbon-based group, for example a $C_1$-$C_{20}$ alkyl group, and Q$^-$ represents an anionic counterion such as a halide ion, for instance fluoride, chloride, bromide or iodide.

In particular, the amino silicones corresponding to the definition of formula (III) are chosen from the compounds corresponding to formula (IV) below:

$$\text{R—Si(CH}_3)_2\text{—O—[Si(CH}_3)_2\text{—O]}_n\text{—[Si(R')(A-NH-(CH}_2)_2\text{-NH}_2)\text{—O]}_m\text{—Si(CH}_3)_2\text{—R''} \quad (IV)$$

in which formula (IV):
R, R' and R", which may be identical or different, denote a $C_1$-$C_4$ alkyl group, preferably methyl, a $C_1$-$C_4$ alkoxy group, preferably methoxy, or hydroxyl,
A represents a linear or branched $C_3$-$C_8$ and preferably $C_3$-$C_6$ alkylene group,
m and n are integers that are dependent on the molecular weight and whose sum is between 1 and 2000 inclusive.

According to a particular embodiment of the invention, the amino silicones are of formula (IV) in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000 g/mol inclusive. The compounds of this type are named "amodimethicone" in the CTFA dictionary.

According to another particular embodiment of the invention, the amino silicones are of formula (IV) in which R, R' and R", which may be identical or different, each represent a $C_1$-$C_4$ alkoxy or hydroxyl group, at least one of the groups R or R" is an alkoxy group and A represents a $C_3$ alkylene group. The hydroxyl/alkoxy mole ratio is preferably between 0.2/1 and 0.4/1 inclusive and advantageously equal to 0.3/1.

Moreover, m and n are such that the weight-average molecular mass of the compound is between 2000 and $10^6$ inclusive. More particularly, n is between 0 and 999 and m is between 1 and 1000 inclusive, the sum of n and m being between 1 and 1000 inclusive.

In this category of compounds, mention may be made, inter alia, of the product Belsil® ADM 652 sold by the company Wacker.

According to another particular embodiment of the invention, the amino silicones are of formula (IV) in which R and R", which are different, each represent a $C_1$-$C_4$ alkoxy or hydroxyl group, at least one of the groups R or R" being an alkoxy group, R' representing a methyl group and A representing a $C_3$ alkylene group. The hydroxyl/alkoxy mole ratio is preferably between 1/0.8 and 1/1.1 inclusive and is advantageously equal to 1/0.95. Moreover, m and n are such that the weight-average molecular mass of the compound is between 2000 and 200 000 inclusive. More particularly, n is between 0 and 999 inclusive and m is between 1 and 1000 inclusive, the sum of n and m being between 1 and 1000.

More particularly, mention may be made of the product Fluid WR® 1300 sold by the company Wacker.

Mention may also be made of the product Belsil AMD Log 1 from Wacker.

Among the amino silicones of formula (IV), mention may also be made of the product Xiameter MEM-8299 from Dow Corning.

It is noted that the molecular mass of these silicones is determined by gel permeation chromatography (room temperature, polystyrene standard, μ styragem columns, eluent THF, flow rate of 1 mm/minute, 200 μl of a solution containing 0.5% by weight of silicone in THF are injected, and detection is performed by refractometry and UV-metry).

According to a particularly advantageous embodiment of the invention, the amino silicone(s) are of formula (III), and in particular the amino silicone of the composition that may be used in the process according to the invention is the polymer known in the CTFA dictionary as trimethylsilyl amodimethicone, corresponding to formula (V) below:

$$(CH_3)_3SiO\text{—}[Si(CH_3)_2O]_n\text{—}[Si(CH_2CHCH_3CH_2NH(CH_2)_2NH_2)O]_m\text{—Si(CH}_3)_3 \quad (V)$$

in which formula (V) n and m have the meanings given above in accordance with formula (III).

Such compounds are described, for example, in patent EP 95238. A compound of formula (III) is sold, for example, under the name Q2-8220 by the company OSI.

(b) the compounds corresponding to formula (VI) below:

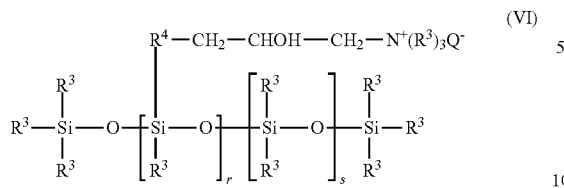

in which formula (VI):
- $R^3$ represents a monovalent $C_1$-$C_{18}$ hydrocarbon-based group, and in particular a $C_1$-$C_{18}$ alkyl or $C_2$-$C_{18}$ alkenyl group, for example methyl;
- $R^4$ represents a divalent hydrocarbon-based group, especially a $C_1$-$C_{18}$ alkylene group or a divalent $C_1$-$C_{18}$, for example $C_1$-$C_8$, alkyleneoxy group;
- $Q^-$ represents an anionic counterion such as halide ions, especially chloride;
- r represents a mean statistical value from 2 to 20 and in particular from 2 to 8;
- s represents a mean statistical value from 20 to 200 inclusive and in particular from 20 to 50 inclusive;

(c) quaternary ammonium silicones, especially of formula (VII):

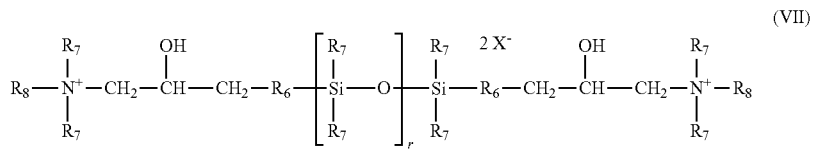

in which formula (VII):
- $R_6$ represents a divalent hydrocarbon-based group, especially a $C_1$-$C_{18}$ alkylene group or a divalent $C_1$-$C_{18}$, for example $C_1$-$C_8$, alkyleneoxy group linked to the Si atom via an SiC bond;
- $R_7$, which may be identical or different, represent a monovalent hydrocarbon-based group containing from 1 to 18 carbon atoms, and in particular a $C_1$-$C_{18}$ alkyl group, a $C_2$-$C_{18}$ alkenyl group or a ring comprising 5 or 6 carbon atoms, for example methyl;
- $R_8$, which may be identical or different, each represent a hydrogen atom, a monovalent hydrocarbon-based group containing from 1 to 18 carbon atoms, and in particular a $C_1$-$C_{18}$ alkyl group, a $C_2$-$C_{18}$ alkenyl group or a group —$R_6$—N(H)—C(O)—$R_7$ with $R_6$ and $R_7$ as defined previously;
- $X^-$, which may be identical or different, represents an anionic counterion such as a halide ion, especially chloride or an anionic counterion derived from an organic acid such as ($C_1$-$C_6$)alkylcarboxylate;
- r represents a mean statistical value between 2 and 200 inclusive and in particular between 5 and 100;

(d) the amino silicones of formula (VIII):

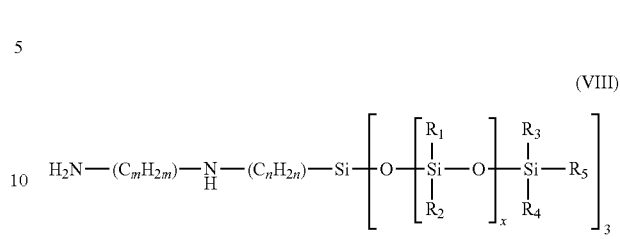

in which formula (VIII):
- $R_1$, $R_2$, $R_3$ and $R_4$, which may be identical or different, each denote a $C_1$-$C_4$ alkyl group or an aryl group such as phenyl,
- $R_5$ denotes a $C_1$-$C_4$ alkyl group or a hydroxyl group,
- n and m, which may be identical or different, represent an integer between 1 and 5 inclusive, and
- x is such that the amine number is between 0.01 and 1 meq/g;

(e) the amino silicones bearing polyalkoxylene groups of formula (IX):

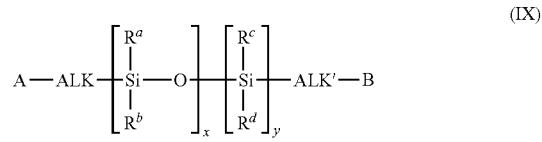

in which formula (IX):
- $R^a$, $R^b$, $R^c$ and $R^d$, which may be identical or different, represent a hydroxyl group or a linear or branched ($C_1$-$C_{10}$)alkyl group, preferably $R^a$, $R^b$, $R^c$ and $R^d$ represent a ($C_1$-$C_6$)alkyl group, more particularly a linear group such as methyl;
- ALK and ALK', which may be identical or different, represent a linear or branched ($C_1$-$C_{10}$)alkylene group, preferably a linear group such as propylene;
- A and B, which may be identical or different, represent an aminopolyalkoxy group below:

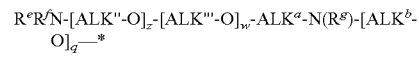

with:
* representing the point of attachment of the radical to the rest of the molecule via ALK or ALK';

$R^e$, $R^f$ and $R^g$, which may be identical or different, representing a hydrogen atom or a linear or branched ($C_1$-$C_{10}$)alkyl group, preferably $R^e$, $R^f$ and $R^g$ represent a hydrogen atom;

ALK" and ALK''', which may be identical or different, represent a linear or branched ($C_1$-$C_{10}$)alkylene and preferably $C_2$ or $C_3$ alkylene group; more particularly, ALK" represents a divalent group —$CH_2$—CH($CH_3$)— and ALK''' represents an ethylene group;

$ALK^a$ and $ALK^b$, which may be identical or different, represent a linear or branched ($C_1$-$C_{10}$)alkylene, preferably $C_2$ or $C_3$, alkylene group, which is optionally substituted, preferably with a hydroxyl group; more particularly, $ALK^a$ represents an ethylene or propylene group or a divalent group —$CH_2$—CH($CH_3$)— and $ALK^b$ represents a divalent group —$CH_2$—CH(OH)—$CH_2$—;

q, which may be identical or different, represent 0 or 1, preferably 1;

w, which may be identical or different, represent an integer, preferably the sum of the w values (w of A+w of B) having a mean value of between 10 and 100 inclusive, more particularly between 20 and 60 inclusive, more preferentially between 30 and 50, such as 40-41;

z, which may be identical or different, represent an integer, preferably the sum of the z values (z of A+z of B) having a mean value of between 1 and 20 inclusive, more particularly between 1 and 10 inclusive, more preferentially between 2 and 5, such as 3;

(f) amino silicones bearing polyalkoxylene groups constituted of polysiloxane blocks and of polyalkoxylene blocks comprising at least one amine group, in particular:

those of formula (X):

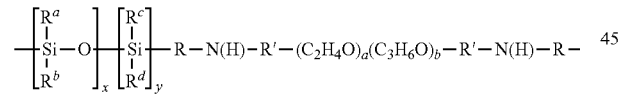

in which formula (X):

$R^a$, $R^b$, $R^c$ and $R^d$, which may be identical or different, represent a hydroxyl group or a linear or branched ($C_1$-$C_{10}$) alkyl group, preferably $R^a$, $R^b$, $R^c$ and $R^d$ represent a ($C_1$-$C_4$)alkyl group, more particularly a linear group such as methyl;

R, which may be identical or different, represent a linear or branched $C_2$-$C_6$ alkylene radical, which is optionally hydroxylated and optionally interrupted with an oxygen atom;

a and b, which may be identical or different, represent a number ranging from 0 to 100;

R', which may be identical or different, represent a hydrogen atom or a $C_1$-$C_4$ alkyl radical such as a methyl radical;

x denotes an integer ranging from 1 to 500 and y denotes an integer ranging from 1 to 10;

those containing units of formula (XI)

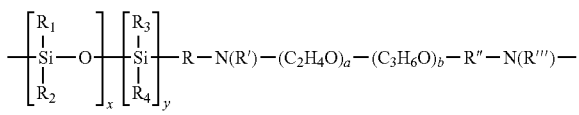

in which formula (XI):

$R_1$ to $R_4$, which may be identical or different, represent a $C_1$-$C_4$ alkyl radical, and preferably methyl;

R and R", which may be identical or different, represent a linear or branched $C_2$-$C_6$ alkylene radical, which is optionally hydroxylated and optionally interrupted with an oxygen atom;

a and b, which may be identical or different, represent an integer ranging from 0 to 100;

R' and R''', which may be identical or different, represent a hydrogen atom or a $C_1$-$C_4$ alkyl radical such as a methyl radical; and x denotes a number ranging from 1 to 500 and y denotes a number ranging from 1 to 10;

those containing units of formula (XII) or of formula (XIII)

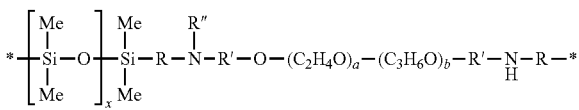

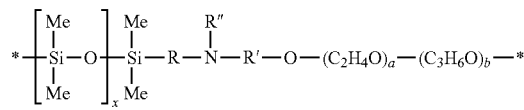

in which formulae (XII) and (XIII):

R, which may be identical or different, represent a linear or branched divalent $C_2$-$C_{12}$ alkyl radical, optionally comprising one or more heteroatoms such as oxygen, preferably R, which may be identical or different, represent an ethylene radical, a linear or branched propylene radical, a linear or branched butylene radical or a radical —$CH_2CH_2CH_2OCH(OH)CH_2$—, more preferentially, R represents a radical —$CH_2CH_2CH_2OCH(OH)CH_2$—;

R', which may be identical or different, represent a linear or branched divalent $C_2$-$C_{12}$ alkyl radical, optionally comprising one or more heteroatoms such as oxygen, preferably R', which may be identical or different, represent an ethylene radical, a linear or branched propylene radical, a linear or branched butylene radical or a radical —$CH_2CH_2CH_2OCH(OH)CH_2$—, more preferentially, R represents a radical —CH($CH_3$)—$CH_2$—;

R" represents a hydrogen atom or a methyl radical;

x denotes an integer ranging from 1 to 10 000, preferably ranging from 10 to 5000;

a represents an integer greater than or equal to 1, preferably ranging from 5 to 200, more preferentially ranging from 10 to 100;

b represents an integer ranging from 0 to 200, preferably ranging from 4 to 100 and preferentially ranging from 5 to 30.

Preferably, in the group of amino silicones (f), the polysiloxane block(s) represent from 50 mol % to 95 mol %, preferably from 70 mol % to 85 mol %, relative to the total weight of the amino silicone.

Preferably, in the group of amino silicones (f), the amine content ranges from 0.02 to 0.5 meq., preferably from 0.05 to 0.2 meq. per gram of copolymer in a dipropylene glycol solution containing 30% by weight of copolymer.

Preferably, in the group of amino silicones (f), the weight-average molecular mass (Mw) of the amino silicones ranges from 5000 to 1 000 000 g/mol, preferably ranges from 10 000 to 200 000 g/mol.

As amino silicones (f), mention may be made especially of the silicones sold under the name Silsoft A-843 or Silsoft A+ by the company Momentive.

Preferably, the amino silicone(s) (compound(s) c)) that may be used in the process according to the invention are chosen from the silicones of formulae (IV), (VIII), (XI), (XII) and (XIII).

In the composition that may be used according to the invention, the amino silicone(s) preferably represent from 0.1% to 4% by weight and preferably from 0.5% to 3% by weight, relative to the total weight of the composition.

The composition that may be used in the process according to the invention may also comprise one or more thickeners.

According to the present invention, the term "thickener" means compounds which, by their presence, increase the viscosity of the composition into which they are introduced by at least 20 cps and preferably by at least 50 cps, at 25° C. and at a shear rate of 1 s$^{-1}$ (the viscosity may be measured using a cone/plate viscometer, a Haake R600 rheometer or the like).

These thickeners are generally nonionic, cationic or amphoteric polymers and are preferably water-soluble or water-dispersible at a pH of 7 and at room temperature (25° C.).

The terms "water-soluble" and "water-dispersible" refer to a polymer which forms in water at a weight concentration of 0.1% at pH 7 and at room temperature (25° C.) a visually homogeneous (one-phase) medium.

Particularly preferably, the thickener(s) are chosen from saccharide-based thickeners.

For the purposes of the present invention, the term "saccharide-based" refers to a polymer constituted of units derived from a carbohydrate of formula $C_n(H_2O)_{n-1}$ or $(CH_2O)_n$, which may be optionally modified by substitution and/or by oxidation and/or by dehydration.

The units may especially be derived from the following carbohydrates: glucose, galactose, arabinose, rhamnose, mannose, xylose, fucose, anhydrogalactose, galacturonic acid, glucuronic acid, mannuronic acid, galactose sulfate, anhydrogalactose sulfate and fructose.

The saccharide-based thickeners that may be used according to the invention may be chosen especially from nonionic or cationic associative saccharide-based thickening polymers and nonionic non-associative saccharide-based thickening polymers.

The term "associative polymers" means polymers that are capable, in an aqueous medium, of reversibly combining with each other or with other molecules.

Associative polymers more particularly comprise at least one hydrophilic part and at least one hydrophobic part.

Thus, in particular, associative polymers comprise at least one hydrophobic group.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based chain is derived from a monofunctional compound.

By way of example, the hydrophobic group may be derived from a fatty alcohol such as stearyl alcohol, dodecyl alcohol or decyl alcohol. It may also denote a hydrocarbon-based polymer, for instance polybutadiene.

The associative saccharide-based thickening polymers that may be used according to the invention are especially chosen from:

(i) nonionic amphiphilic saccharide-based polymers comprising at least one fatty chain and at least one hydrophilic unit;

(ii) cationic amphiphilic saccharide-based polymers comprising at least one hydrophilic unit and at least one fatty-chain unit, the fatty chains containing from 10 to 30 carbon atoms.

The nonionic associative polymers are preferably chosen from:

(1) celluloses modified with groups comprising at least one fatty chain; examples that may be mentioned include:
  hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS ($C_{16}$ alkyls) sold by the company Aqualon, or the product Bermocoll EHM 100 sold by the company Berol Nobel,
  hydroxyethylcelluloses modified with alkylphenyl polyalkylene glycol ether groups, such as the product Amercell Polymer HM-1500 (nonylphenyl polyethylene glycol (15) ether) sold by the company Amerchol, (2) hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia.

The cationic associative saccharide-based polymers are preferably chosen from quaternized cellulose derivatives.

The quaternized cellulose derivatives are, in particular:

i) quaternized celluloses modified with groups comprising at least one fatty chain, such as linear or branched alkyl, linear or branched arylalkyl or linear or branched alkylaryl groups comprising at least 8 carbon atoms, or mixtures thereof;

ii) quaternized hydroxyethylcelluloses modified with groups comprising at least one fatty chain, such as linear or branched alkyl, linear or branched arylalkyl or linear or branched alkylaryl groups comprising at least 8 carbon atoms, or mixtures thereof;

iii) the hydroxyethylcelluloses of formula (XIV):

(XIV)

[Chemical structure showing hydroxyethylcellulose derivative with $-(CH_2CH_2O)_x-$ groups and $-[C H_2-C H-C H]_y-$ repeating units with R and R' substituents]

in which formula (XIV):

R and R', which may be identical or different, represent an ammonium group such as $R_aR_bR_cN^+\text{—}$, $Q^-$ in which $R_a$, $R_b$ and $R_c$, which may be identical or different, represent a hydrogen atom or a linear or branched $C_1$-$C_{30}$ and preferentially $C_1$-$C_{20}$ alkyl group, such as methyl or dodecyl; and $Q^-$ represents an anionic counterion such as a halide, for instance a chloride or bromide;

n, x and y, which may be identical or different, represent an integer between 1 and 10 000.

The alkyl radicals borne by the above quaternized celluloses i) or hydroxyethylcelluloses ii) preferably comprise from 8 to 30 carbon atoms.

The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol and the products Crodacel QM®, Crodacel QL® ($C_{12}$ alkyl) and Crodacel QS® ($C_{18}$ alkyl) sold by the company Croda.

Mention may also be made of the hydroxyethylcelluloses of formula (XIV) in which R represents a trimethylammonium halide and R' represents a dimethyldodecylammonium halide, more preferentially R represents trimethylammonium chloride $(CH_3)_3N^+\ Cl^-$ and R' represents dimethyldodecylammonium chloride $(CH_3)_2(C_{12}H_{25})N^+\ Cl^-$. Polymers of this type are known under the trade name softCAT Polymer SL®, such as SL-100 and SL-60.

More particularly, the polymers of formula (XIV) are those whose viscosity is between 2000 and 3000 cPs inclusive. Preferentially, the viscosity is between 2700 and 2800 cPs inclusive.

As explained previously, the saccharide-based thickeners may be chosen from nonionic non-associative saccharide-based thickening polymers.

As nonionic non-associative saccharide-based thickening polymers that may be used according to the invention, mention may be made more particularly of native gums such as:

1) tree or shrub exudates, preferably:
gum arabic (branched polymer of galactose, arabinose, rhamnose and glucuronic acid);
ghatti gum (polymer derived from arabinose, galactose, mannose, xylose and glucuronic acid);
karaya gum (polymer derived from galacturonic acid, galactose, rhamnose and glucuronic acid);
gum tragacanth (polymer of galacturonic acid, galactose, fucose, xylose and arabinose);

2) gums derived from algae, preferably:
agar (polymer derived from galactose and anhydrogalactose);
alginates (polymers of mannuronic acid and of glucuronic acid);
carrageenans and furcellerans (polymers of galactose sulfate and of anhydrogalactose sulfate);

3) gums derived from seeds or tubers, preferably:
guar gum (polymer of mannose and galactose);
locust bean gum (polymer of mannose and galactose);
fenugreek gum (polymer of mannose and galactose);
tamarind gum (polymer of galactose, xylose and glucose);
konjac gum (polymer of glucose and mannose);

4) microbial gums, including:
xanthan gum (polymer of glucose, mannose acetate, mannose/pyruvic acid and glucuronic acid);
gellan gum (polymer of partially acylated glucose, rhamnose and glucuronic acid);
scleroglucan gum (glucose polymer);

5) plant extracts, preferably:
cellulose (glucose polymer);
starch (glucose polymer) and
inulin.

These nonionic non-associative saccharide-based thickening polymers may be physically or chemically modified.

As physical treatment, mention may especially be made of the temperature.

Chemical treatments that may be mentioned include esterification, etherification, amidation and oxidation reactions.

These treatments can afford polymers that may especially be nonionic, anionic or amphoteric.

Preferably, these chemical or physical treatments are applied to guar gums, locust bean gums, starches and celluloses.

The nonionic guar gums that may be used according to the invention may be modified with $C_1$-$C_6$ (poly)hydroxyalkyl groups.

Among the $C_1$-$C_6$ (poly)hydroxyalkyl groups, mention may be made, for example, of hydroxymethyl, hydroxyethyl, hydroxypropyl and hydroxybutyl groups.

These modified guar gums are well known in the prior art and may be prepared, for example, by reacting the corresponding alkene oxides, for instance propylene oxides, with native guar gum so as to obtain a guar gum modified with hydroxypropyl groups.

The degree of hydroxyalkylation preferably varies from 0.4 to 1.2 and corresponds to the number of alkylene oxide molecules consumed by the number of free hydroxyl functional groups present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The nonionic starches that may be used according to the invention may be chemically or physically modified especially by one or more of the following reactions: pregelatinization, oxidation, crosslinking, esterification, etherification, amidation, heat treatments.

As modified starches that may be used according to the invention, mention may preferably be made of distarch phosphates or compounds rich in distarch phosphate, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

Mention may also be made of amphoteric starches, these amphoteric starches comprising one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups can be of primary, secondary, tertiary or quaternary amine type.

The native starch molecules used in the present invention may originate botanically from cereals or tubers especially such as corn, potato, oat, rice, tapioca, sorghum, barley, wheat, cassava or pea.

The starch is preferably derived from potato.

It is also possible to use the hydrolysates of the starches mentioned above.

The celluloses that may be used according to the invention may be chemically or physically modified.

Modified celluloses that may be mentioned more particularly include cellulose polymers not comprising any $C_{10}$-$C_{30}$ fatty chains in their structure.

Thus, the cellulose polymers that may be used according to the invention may be chosen from unsubstituted celluloses, including those in a microcrystalline form, and cellulose ethers.

The modified celluloses that may be used according to the present invention may be cationic, amphoteric or nonionic.

Among these cellulose-based polymers, cellulose ethers, cellulose esters and cellulose ester ethers are distinguished.

The cellulose ethers that may be used according to the present invention may more particularly be nonionic or cationic.

Among the nonionic cellulose ethers not bearing a $C_{10}$-$C_{30}$ fatty chain, i.e. "non-associative", mention may be made of ($C_1$-$C_4$)alkylcelluloses, such as methylcelluloses and ethylcelluloses (for example, Ethocel standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$)alkyl-($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

Among the cationic cellulose ethers without a fatty chain, mention may be made of cationic cellulose derivatives such as cellulose copolymers or cellulose derivatives grafted with a water-soluble quaternary ammonium monomer, and described in particular in U.S. Pat. No. 4,131,576, such as (poly)hydroxy($C_1$-$C_4$)alkyl celluloses, for instance hydroxymethyl-, hydroxyethyl- or hydroxypropylcelluloses grafted especially with a methacryloylethyltrimethylammonium, methacrylamidopropyltrimethylammonium or dimethyldiallylammonium salt. The commercial products corresponding to this definition are more particularly the products sold under the names Celquat L 200® and Celquat H 100® by the company National Starch.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates.

Among the cellulose ester ethers, mention may be made of hydroxypropylmethylcellulo se phthalates and ethylcellulose sulfates.

The composition that may be used in the process according to the invention may also comprise one or more additional compounds chosen from surfactants, preferably chosen from nonionic, anionic, cationic and amphoteric surfactants, fixing polymers, conditioning agents preferably chosen from cationic polymers, silicones other than the compounds c), chitosans other than the saccharide-based thickeners mentioned previously, and derivatives of these compounds, UV-screening agents, fillers such as nacres, titanium dioxide, resins and clays, fragrances, peptizers, vitamins, preserving agents, acidic agents, alkaline agents, reducing agents, oxidizing agents, direct dyes, in particular those chosen from cationic and natural direct dyes, oxidation dyes, and a mixture of these compounds.

The above additional compounds may be present in an amount ranging from 0% to 20% by weight relative to the total weight of the composition that may be used according to the invention.

The composition that may be used in the process according to the invention may also comprise one or more solvents chosen in particular from hydrophilic solvents and hydrophobic solvents.

Examples of hydrophilic solvents that may be mentioned include linear or branched, preferably saturated monoalcohols, comprising 2 to 10 carbon atoms, such as ethyl alcohol, isopropyl alcohol, and aromatic alcohols such as phenylethyl alcohol; alone or as a mixture.

The above solvents may be present in an amount ranging from 0.01% to 50% by weight relative to the total weight of the composition that may be used according to the invention.

The composition that may be used in the process according to the invention advantageously comprises water, which advantageously represents from 1% to 95%, preferably from 20% to 90% and more preferentially from 40% to 85% by weight relative to the total weight of the composition.

The composition that may be used in the process according to the invention may be in the form of a wax, a paste, a cream, a gel, a foam, a spray or a lotion.

The process according to the invention comprises, preferably after the step of applying the composition, a step of heat treatment of the keratin fibres.

The step of heat treatment of the keratin fibres is generally performed at a temperature ranging from 40 to 250° C., preferably ranging from 90° C. to 250° C. and more preferentially ranging from 180° C. to 230° C.

Preferably, the heat treatment step has a duration ranging from 5 seconds to 1 hour, preferably ranging from 5 seconds to 1 minute, per lock of hair.

This heat treatment step is generally performed using a heating tool such as a straightening iron, a curling iron, a crimping iron, a waving iron, a hood, a hairdryer, an infrared heating system or a heating roller.

In a first embodiment of the process according to the invention, the composition is applied to a wet or dry head of hair, preferably dry hair, with or without a leave-on time. The bath ratio of the applied formulation may range from 0.1 to 10 and more particularly from 0.2 to 5. The keratin fibres are then optionally rubbed dry, preferably rubbed dry. One or more heating means are applied once or in succession to the keratin fibres at a temperature ranging from 40 to 250° C., preferably from 90 to 250° C. and better still from 180 to 230° C. for a time ranging from 5 seconds to 1 hour and preferably from 5 seconds to 1 minute, per lock of hair.

The hair then optionally undergoes one or more of the following operations: rinsing, shampooing and treatment with a rinse-out hair conditioner, drying, preferably using a hood or a hairdryer.

In general and preferably in the process according to the invention, the step of application to the keratin fibres is performed on dry keratin fibres.

Preferably, when a leave-on time is observed, said leave-on time is preferably from 5 minutes to 1 hour.

For the purposes of the present invention, the term "bath ratio" means the ratio between the total weight of the applied composition and the total weight of keratin fibres to be treated.

In a second embodiment, the process according to the invention is performed one or more times, optionally spaced by one or more cosmetic treatments, preferably spaced by one or more shampoo washes, to treat hair that has regrown or that has undergone other treatments liable to cause changes in the curliness, or to obtain the desired shape or the desired shape intensity.

Preferably, the process according to the invention does not comprise the application of a reducing composition either before or during or after the application of the composition that may be used in the process according to the invention.

This is particularly advantageous in the context of the invention since it makes it possible to perform a process that is sparingly aggressive to the hair.

As explained previously, another subject of the present invention is a composition comprising:

a) one or more compounds chosen from urea and/or urea derivatives, preferably present in a content ranging from 1% to 15% by weight, relative to the total weight of the composition, b) one or more polyols, c) one or more amino silicones, preferably present in a content ranging from 0.1% to 4% by weight, relative to the total weight of the composition, the compound(s) b)/compound(s) a) weight ratio preferably being greater than or equal to 0.5.

The composition according to the invention may comprise one or more of the characteristics of the composition used in the process according to the invention as described above.

In particular, the composition according to the invention may comprise one or more of the characteristics concerning urea and/or urea derivatives, the polyol(s), the amino silicone(s), the optional thickener(s), and the additional compound(s) optionally present.

The examples that follow serve to illustrate the invention without, however, being limiting in nature.

EXAMPLES

Example 1

Comparative composition 1 and compositions 2 and 3 according to the invention, which may be used in the process according to the invention, were prepared on the basis of the formulations indicated in Table 1 below, in which the amounts are expressed as weight percentages relative to the total weight of the composition.

TABLE 1

| | Compositions | | |
|---|---|---|---|
| Ingredients | 1 | 2 | 3 |
| Urea | 10 | 10 | 10 |
| Ethanol | 10 | 10 | 10 |
| 1,3-Propanediol | 10 | 10 | 10 |
| Amodimethicone and Trideceth-5 and Trideceth-10[(1)] | — | — | 6.67 |
| Amodimethicone and Trideceth-6 and cetrimonium chloride[(2)] | — | 1.68 | — |
| Water | qs 100 | qs 100 | qs 100 |

[(1)]Polydimethylsiloxane bearing aminoethyl iminopropyl groups as a nonionic microemulsion containing 17% AM (Belsil AMD Log 1 from Wacker).
[(2)]Polydimethylsiloxane bearing aminoethyl aminopropyl groups, bearing a methoxy and/or hydroxyl function and alpha-omega silanols, as a cationic 60% aqueous emulsion (Xiameter MEM-8299 from Dow Corning)

The straightening process used in this example is as follows:
shampooing then drying of the locks of hair studied,
application of one of the compositions of Table 1 to dry hair (bath ratio=1:1)
leave-on time: 5 min
blow-drying: 15 passes (maximum power)
straightening iron: 5 slow passes (6 sec/20 cm) per lock at 230° C. for locks of 1 to 1.5 g (on average 1.35 g).
Starting locks: Natural curly type IV Caucasian The locks of hair undergo 1 and 5 shampoo washes in order to evaluate the persistence over time of the straightening processes.

The curl relaxation quality and the volume control are evaluated visually after one shampoo wash and after five shampoo washes.

The processes according to the invention (compositions 2 and 3) afford better curl relaxation and also better volume control than the comparative process not comprising the application of a composition comprising an amino silicone. In particular, the curl relaxation is complete from the very first shampoo wash and persistent over the following shampoo washes.

Furthermore, the processes according to the invention make it possible to give the hair better cosmeticity. The locks have a smoother feel, down to the ends.

Example 2

Comparative composition 4 and composition 5 according to the invention, which may be used in the process according to the invention, were prepared on the basis of the formulations indicated in Table 2 below, in which the amounts are expressed as weight percentages of active matter relative to the total weight of the composition.

TABLE 2

| | Compositions | |
|---|---|---|
| Ingredients | 4 | 5 |
| Urea | 10 | 10 |
| Ethanol | 10 | 10 |
| 1,3-Propanediol | 10 | 10 |
| Amodimethicone and Trideceth-5 and Trideceth-10[(1)] | — | 1 |
| Levulinic acid | 10 | 10 |
| Water | qs 100 | qs 100 |

[(1)]Polydimethylsiloxane bearing aminoethyl iminopropyl groups as a nonionic microemulsion containing 17% AM (Belsil AMD Log 1 from Wacker).

The straightening process used in this example is as follows:
shampooing then drying of the locks of hair studied,
application of one of the compositions of Table 2 to dry hair (bath ratio=1:1)
leave-on time: 30 min
blow-drying: 15 passes with a brush (with the maximum power of the hair dryer)
straightening iron: 10 slow passes (6 sec/20 cm) per lock at 210° C. for locks of 1 to 1.5 g (on average 1.35 g).
Starting locks: Natural curly type IV Caucasian The locks of hair undergo 1 and 10 shampoo washes in order to evaluate the persistence over time of the straightening processes.

The curl relaxation quality and the volume control are evaluated visually by comparative pictures after one shampoo wash and after ten shampoo washes. The curls are washed with a classical shampoo (DOP Camomille), rinsed, then air dried.

The curls are vertically suspended then pictured.

The coefficient of straightening is calculated: it corresponds to the ratio length/width of the locks of hair.

Picture T corresponds to a lock of hair before the process (natural curly type IV Caucasian)

Pictures D1 and D10 correspond to locks of hair treated with the composition D (comparative) after one shampoo (D1) and ten shampoos (D10).

Pictures E1 and E10 correspond to locks of hair treated with the composition E (invention) after one shampoo (E1) and ten shampoos (E10).

The length/width measures and the coefficient of straightening are given in the table 3 below.

TABLE 3

| | | D | E |
|---|---|---|---|
| 1 shampoo | Length | 18.75 | 19.8 |
| | Width | 5.31 | 4.52 |
| | Coefficient of straightening | 3.53 | 4.38 |
| 10 shampoo | Length | 17.78 | 19.2 |
| | Width | 4.52 | 2.8 |
| | Coefficient of straightening | 3.93 | 6.86 |

The composition E according to the invention and which can be used in the process according to the invention has been able to improve the sustainability of straightening in comparison with the comparative composition D.

In particular, the locks of hair treated with the composition E are straight-lined (see pictures E). The locks of hair treated with the composition D have undulations (see pictures D).

This improvement is visible after one shampoo and also after ten shampoos.

The invention claimed is:

1. A process for treating keratin fibres, the process comprising:
    1) applying to the keratin fibres a straightening composition comprising:
        a) at least one compound chosen from urea and/or urea derivatives,
        b) at least one polyol,
        c) at least one amino silicone, and
        d) at least one hydrophilic solvent chosen from ethyl alcohol, isopropyl alcohol, or a mixture thereof;
        wherein the weight ratio of the at least one compound b) to the at least one compound a) is greater than or equal to 1; and
    2) heat treating the keratin fibres,
    wherein the heat treating of the keratin fibres is performed at a temperature ranging from 90° C. to 250° C.,
    and wherein the process does not comprise a step of applying a reducing composition before, during or after the application of said straightening composition.

2. The process according to claim 1, wherein said at least one compound a) is chosen from the compounds of formula (I) or (II), salts thereof, or hydrates thereof:

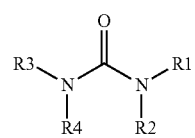

(I)

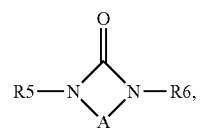

(II)

wherein:
R1, R2, R3 and R4 are each chosen from, independently:
(i) a hydrogen atom or
(ii) a linear or branched, cyclic or acyclic $C_1$-$C_5$ lower alkyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, ($C_1$-$C_4$)alkyl, (di)($C_1$-$C_4$)(alkyl)amino, preferably dimethylamino, carboxyl, halogen, $C_6$-$C_{18}$ aryl, carboxamide, or N-methylcarboxamide;
with the proviso that:
when R1, R2 and R3 represent a hydrogen atom, R4 may be chosen from: carboxamide, methoxy, ethoxy, 1,2,4-triazolyl, cyclopentyl, ($C_1$-$C_6$)alkylcarbonyl, acetyl, ($C_1$-$C_6$)alkoxycarbonyl, methoxycarbonyl, ethoxycarbonyl, CO—CH═CH—COOH, phenyl optionally substituted with a chlorine atom or a hydroxyl, benzyl, or 2,5-dioxo-4-imidazolidinyl radical;
when R1 and R3 represent a hydrogen atom, R2 may represent a hydrogen atom or a methyl or ethyl radical and R4 may represent an acetyl radical;
when R1 and R2 represent a hydrogen atom, R3 and R4 can form, with the nitrogen atom that bears them, a 5- or 6-membered ring, piperidine, 3-methylpyrazole, 3,5-dimethylpyrazole, or maleimide ring;
R1 and R2 and also R3 and R4 can form, with the nitrogen atom that bears them, an imidazole ring;
R5 and R6 are chosen from, independently of each other:
(iii) a hydrogen atom or
(iv) a linear or branched, cyclic or acyclic $C_1$-$C_5$ lower alkyl, acyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, amino, dimethylamino, carboxyl, halogen, $C_6$-$C_{18}$ aryl, carboxamide, or N-methylcarboxamide;
A is a radical chosen from the following radicals: $CH_2$—$CH_2$, CH═CH, $CH_2$—CO, CO—NH, CH═N, CO—CO, CHOH—CHOH, (HOOC)CH—CH, CHOH—CO, $CH_2$—$CH_2$—$CH_2$, $CH_2$—NH—CO, CH═C($CH_3$)—CO, NH—CO—NH, $CH_2$—$CH_2$—CO, $CH_2$—N($CH_3$)—$CH_2$, NH—$CH_2$—NH, CO—CH($CH_3$)—$CH_2$, CO—$CH_2$—CO, CO—NH—CO, CO—CH(COOH)—$CH_2$, CO—CH═C(COOH), CO—CH═C($CH_3$), CO—C($NH_2$)═CH, CO—C($CH_3$)═N, CO—CH═CH, CO—CH═N, or CO—N═CH.

3. The process according to claim 2, wherein the at least one compound a) is of formula (I) and is chosen from:
urea
methylurea
ethylurea
propylurea
n-butylurea
sec-butylurea
isobutylurea
tert-butylurea
cyclopentylurea
ethoxyurea
hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleamide
N-carbamoylmaleamic acid
piperidinecarboxamide
1,2,4-triazol-4-ylurea
hydantoic acid
methyl allophanate
ethyl allophanate
acetylurea
hydroxyethyleneurea
2-(hydroxyethyl)ethyleneurea
diallylurea
chloroethylurea
N,N-dimethylurea
N,N-diethylurea
N,N-dipropylurea
cyclopentyl-1-methylurea
1,3-dimethylurea
1,3-diethylurea
1,3-bis(2-hydroxyethyl)urea
1,3-bis(2-hydroxypropyl)urea
1,3-bis(3-hydroxypropyl)urea
1,3-dipropylurea
ethyl-3-propylurea
sec-butyl-3-methylurea
isobutyl-3-methylurea
cyclopentyl-3-methylurea
N-acetyl-N'-methylurea
trimethylurea
butyl-3,3-dimethylurea
tetramethylurea, or
mixtures thereof.

4. The process according to claim 2, wherein the at least one compound a) is of formula (II) and is chosen from:
parabanic acid
1,2-dihydro-3H-1,2,4-triazol-2-one
barbituric acid
uracil
1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidone
1-methyl-2-imidazolidinone
1,3-dimethyl-2-imidazolidinone
4,5-dihydroxyimidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-N-propylhydantoin
5-ethyl-5-methylhydantoin
5-hydroxy-5-methylhydantoin
5-hydroxymethylhydantoin
1-allylhydantoin
1-aminohydantoin
hydantoin-5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
1,3-dimethylbarbituric acid
cyanuric acid
1-methylhexahydropyrimidine-2,4-dione
1,3-dimethyl-3,4,5,6-tetrahydro-2-(1H)-pyrimidinone
5-(hydroxymethyl-2,4-(1H, 3H)-pyrimidinedione
2,4-dihydroxypyrimidine-5-carboxylic acid
6-azathymine
5-methyl-1,3,5-triazinan-2-one
N-carbamoylmaleamic acid
alloxan monohydrate, or
mixtures thereof.

5. The process according to claim 1, wherein the at least one compound a) is chosen from urea, hydroxyethylurea, or mixtures thereof.

6. The process according to claim 1, wherein the total amount of the at least one compound a) ranges from 1% to 15% by weight, relative to the total weight of the straightening composition.

7. The process according to claim 1, wherein the at least one compound b) is chosen from polyols comprising at least three carbon atoms, ethylene glycol, propylene glycol, 1,3- propanediol, 1,3-butylene glycol, 1,2-pentanediol, dipropylene glycol, hexylene glycol, pentylene glycol, glycerol, or a mixture thereof.

8. The process according to claim 1, wherein the total amount of the at least one compound b) ranges from 1% to 30% by weight, relative to the total weight of the straightening composition.

9. The process according to claim 1, wherein the at least one compound c) is chosen from amino silicones comprising at least 4 carbon atoms.

10. The process according to claim 1, wherein the at least one compound c) is chosen from the silicone(s) (a) to (f) below:

(a) the compounds corresponding to formula (III) below:

$(R_1)_a(T)_{3-a}\text{-Si}[OSi(T)_2]_n\text{-}[(OSi(T)_b(R_1)_{2-b}]_m\text{—OSi}(T)_{3-a}\text{-}(R_1)_a$     (III), wherein in formula (III):
  T is chosen from a hydrogen atom or a phenyl, hydroxyl (—OH), $C_1$-$C_8$ alkyl group, methyl, $C_1$-$C_8$ alkoxy, or methoxy,
  a is 0 or an integer from 1 to 3,
  b is 0 or 1,
  m and n are integers such that the sum (n+m) ranges from 1 to 2000, n is a number from 0 to 1999, and m is a number from 1 to 2000,
  $R_1$ is a monovalent group of formula $—C_qH_{2q}L$ in which q is an integer from 2 to 8 inclusive and L is an optionally quaternized amino group chosen from the following groups:
  $N(R_2)—CH_2—CH_2—N(R_8)_2$,
  $N(R_2)_2$,
  $N^+(R_2)_3\ Q^-$,
  $N^+(R_2)(H)_2^-$,
  $N+(R_2)_2HQ^-$,
  $N(R_2)—CH_2—CH_2—N+(R_2)(H)_2\ Q^-$,
  wherein:
    $R_2$ is chosen from a hydrogen atom, a phenyl group, a benzyl group, a saturated monovalent hydrocarbon-based group, or a $C_1$-$C_{20}$ alkyl group, and
    $Q^-$ is chosen from an anionic counterion, a halide ion, fluoride, chloride, bromide, or iodide,
(b) the compounds corresponding to formula (VI) below:

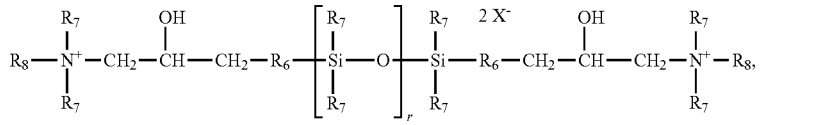

(VI)

wherein in formula (VI):
  $R^3$ is chosen from a monovalent $C_1$-$C_{18}$ hydrocarbon-based group, $C_1$-$C_{18}$ alkyl, $C_2$-$C_{18}$ alkenyl, or methyl;
  $R^4$ is chosen from a divalent hydrocarbon-based group, a $C_1$-$C_{18}$ alkylene group, a divalent $C_1$-$C_{18}$, or $C_1$-$C_8$, alkyleneoxy group;
  $Q^-$ is chosen from an anionic counterion, halide ions, or chloride;
  r represents a mean statistical value from 2 to 20;
  s represents a mean statistical value from 20 to 200;
(c) quaternary ammonium silicones, of formula (VII):

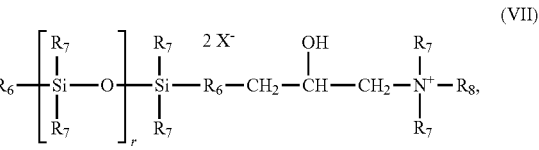

(VII)

wherein in formula (VII):
  $R_6$ is chosen from a divalent hydrocarbon-based group, a $C_1$-$C_{18}$ alkylene group, a divalent $C_1$-$C_{18}$, or $C_1$-$C_8$, alkyleneoxy group linked to the Si atom via an SiC bond;
  $R_7$, which may be identical or different, is chosen from a monovalent hydrocarbon-based group containing from 1 to 18 carbon atoms, a $C_1$-$C_{18}$ alkyl group, a $C_2$-$C_{18}$ alkenyl group, a ring comprising 5 or 6 carbon atoms, or methyl;
  $R_8$, which may be identical or different, are each chosen from a hydrogen atom, a monovalent hydrocarbon-based group containing from 1 to 18 carbon atoms, a $C_1$-$C_{18}$ alkyl group, a $C_2$-$C_{18}$ alkenyl group, or a group $—R_6—N(H)—C(O)—R_7$ with $R_6$ and $R_7$ as defined previously;
  $X^-$, which may be identical or different, is chosen from an anionic counterion, a halide ion, chloride, an anionic counterion derived from an organic acid, or $(C_1$-$C_6)$alkylcarboxylate;
  r represents a mean statistical value between 2 and 200 inclusive;
(d) the amino silicones of formula (VIII):

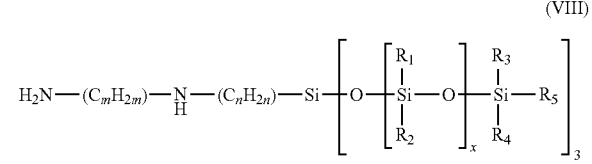

(VIII)

wherein in formula (VIII):
  $R_1$, $R_2$, $R_3$ and $R_4$, which may be identical or different, are each chosen from a $C_1$-$C_4$ alkyl group, an aryl group, or phenyl,
  $R_5$ is chosen from a $C_1$-$C_4$ alkyl group or a hydroxyl group,
  n and m, which may be identical or different, represent an integer between 1 and 5 inclusive, and x is such that the amine number is between 0.01 and 1 meq/g;
(e) the amino silicones bearing polyalkoxylene groups of formula (IX):

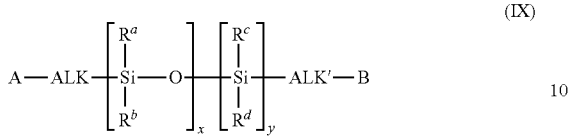

wherein in formula (IX):
$R^a$, $R^b$, $R^c$ and $R^d$, which may be identical or different, are chosen from a hydroxyl group, a linear or branched $(C_1-C_{10})$alkyl group, a $(C_1-C_6)$ alkyl group, or methyl;
ALK and ALK', which may be identical or different, are chosen from a linear or branched $(C_1-C_{10})$ alkylene group, or propylene;
A and B, which may be identical or different, are chosen from an aminopolyalkoxy group below:

$R^eR^fN-[ALK''-O]_z-[ALK'''-O]_w-ALK^a-N(R^g[ALK^b-O]_q-*$, wherein:
represents the point of attachment of the radical to the rest of the molecule via ALK or ALK';
$R^e$, $R^f$ and $R^g$, which may be identical or different, are chosen from a hydrogen atom or a linear or branched $(C_1-C_{10})$alkyl group;
ALK'' and ALK''', which may be identical or different, are chosen from a linear or branched $(C_1-C_{10})$ alkylene, $C_2$ or $C_3$ alkylene group; a divalent group $-CH_2-CH(CH_3)-$, or an ethylene group;
$ALK^a$ and $ALK^b$, which may be identical or different, are chosen from a linear or branched $(C_1-C_{10})$ alkylene, $C_2$ or $C_3$ alkylene group, which is optionally substituted, ethylene, propylene group, a divalent group $-CH_2-CH(CH_3)-$, or a divalent group $-CH_2-CH(OH)-CH_2-$;
q, which may be identical or different, represent 0 or 1;
w, which may be identical or different, represent an integer, wherein the sum of the w values (w of A+w of B) having a mean value of between 10 and 100 inclusive;
z, which may be identical or different, represent an integer, wherein the sum of the z values (z of A+z of B) having a mean value of between 1 and 20 inclusive;
(f) amino silicones bearing polyalkoxylene groups constituted of polysiloxane blocks and of polyalkoxylene blocks comprising at least one amine group, chosen from:
those of formula (X):

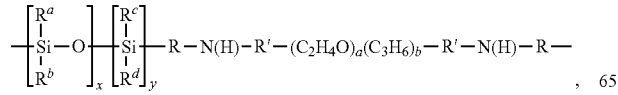

wherein in formula (X):
$R^a$, $R^b$, $R^c$ and $R^d$, which may be identical or different, are chosen from a hydroxyl group, a linear or branched $(C_1-C_{10})$ alkyl group, a $(C_1-C_4)$alkyl group, or methyl;
R, which may be identical or different, is chosen from a linear or branched $C_2-C_6$ alkylene radical, which is optionally hydroxylated and/or optionally interrupted with an oxygen atom;
a and b, which may be identical or different, each represent a number ranging from 0 to 100;
R', which may be identical or different, is chosen from a hydrogen atom, a $C_1-C_4$ alkyl radical, or a methyl radical;
x denotes an integer ranging from 1 to 500 and y denotes an integer ranging from 1 to 10;
those containing units of formula (XI)

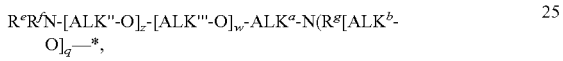

wherein in formula (XI):
$R_1$ to $R_4$, which may be identical or different, are chosen from a $C_1-C_4$ alkyl radical or methyl;
R and R'', which may be identical or different, each represent a linear or branched $C_2-C_6$ alkylene radical, which is optionally hydroxylated and optionally interrupted with an oxygen atom;
a and b, which may be identical or different, each denote an integer ranging from 0 to 100;
R' and R'', which may be identical or different, are chosen from a hydrogen atom, a $C_1-C_4$ alkyl radical, or a methyl radical; and
x denotes a number ranging from 1 to 500 and y denotes a number ranging from 1 to 10;
those containing units of formula (XII) or of formula (XIII)

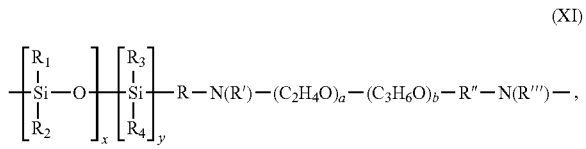

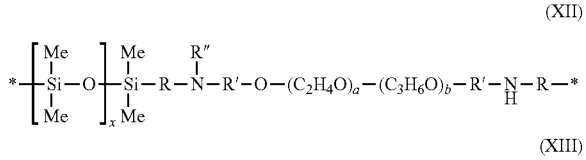

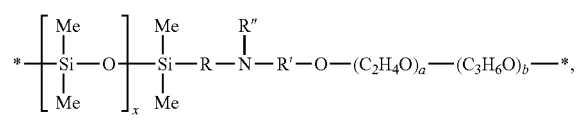

wherein in formulae (XII) and (XIII):
R, which may be identical or different, is chosen from a linear or branched divalent $C_2-C_{12}$ alkyl radical, optionally comprising one or more heteroatoms or oxygen; an ethylene radical; a linear or branched propylene radical; a linear or branched butylene radical; or a radical $-CH_2CH_2CH_2OCH(OH)CH_2-$;
R', which may be identical or different, is chosen from a linear or branched divalent $C_2-C_{12}$ alkyl radical, optionally comprising one or more heteroatoms or oxygen; an ethylene radical; a linear or branched propylene radical; a linear or branched butylene radical, a radical —CH$_2$CH$_2$CH$_2$OCH(OH)CH$_2$—, or a radical —CH(CH$_3$)—CH$_2$—;

R" is chosen from a hydrogen atom or a methyl radical;

x denotes an integer ranging from 1 to 10 000;

a denotes an integer greater than or equal to 1;

b denotes an integer ranging from 0 to 200.

11. The process according to claim 10, wherein the amino silicone is chosen from the silicones of formulae (Ill), (VIII), (XI), (XII), or (XIII).

12. The process according to claim 1, wherein the total amount of the at least one amino silicone ranges from 0.1% to 4% by weight, relative to the total weight of the straightening composition.

13. The process according to claim 1, wherein the straightening composition further comprises at least one thickener.

14. The process according to claim 1, wherein the heat treating of the keratin fibres is performed at a temperature ranging from 180° C. to 230° C.

15. The process according to claim 1, wherein the heat treating step has a duration ranging from 5 seconds to 1 hour, per lock of hair.

* * * * *

UNITED STATES PATENT AND TRADEMARK OFFICE
CERTIFICATE OF CORRECTION

PATENT NO. : 11,400,042 B2  
APPLICATION NO. : 16/064310  
DATED : August 2, 2022  
INVENTOR(S) : Guillaume Ronchard et al.

Page 1 of 1

It is certified that error appears in the above-identified patent and that said Letters Patent is hereby corrected as shown below:

In the Claims

Claim 10, Column 27, Line 64, in formula (X) please change "(C3H6)b" to -- (C3H6O)b --; and Claim 10, Column 28, Line 36, please change "R''" to -- R''' --.

Signed and Sealed this  
Tenth Day of January, 2023

Katherine Kelly Vidal  
*Director of the United States Patent and Trademark Office*